United States Patent [19]

Sodero

[11] Patent Number: 5,405,387
[45] Date of Patent: Apr. 11, 1995

[54] INTRAOCULAR LENS

[76] Inventor: Maria A. Sodero, Via T.Levi Civita, 73100 Tricase (Lecce), Italy

[21] Appl. No.: 134,673

[22] Filed: Oct. 12, 1993

[30] Foreign Application Priority Data

Oct. 13, 1992 [IT] Italy .................................. FI92A0199

[51] Int. Cl.6 ............................................... A61F 2/16
[52] U.S. Cl. .......................................................... 623/6
[58] Field of Search ..................... 623/5, 6; 351/160 R

[56] References Cited

U.S. PATENT DOCUMENTS

| | | | |
|---|---|---|---|
| 4,253,199 | 3/1981 | Banko | 623/6 |
| 4,466,705 | 8/1984 | Michelson | 623/6 X |
| 4,704,122 | 11/1987 | Portnoy | 623/6 |
| 4,731,078 | 3/1988 | Stoy et al. | 623/6 |

FOREIGN PATENT DOCUMENTS

| | | | |
|---|---|---|---|
| 0202049 | 11/1986 | European Pat. Off. | 623/6 |
| 2666735 | 3/1992 | France | 623/6 |
| 2525377 | 12/1976 | Germany | 623/6 |

Primary Examiner—Randall L. Green
Assistant Examiner—Mary Beth Jones
Attorney, Agent, or Firm—Browdy and Neimark

[57] ABSTRACT

An intraocular lens comprising an optic disk (1) and means (4) for securing it to the ocular structure characterized by the fact that said optic disk comprises a first and a second face (1a, 1b) which are coaxial and spaced, of an optically negligeable thickness and different radii of curvature, coupled to delimitate between them a sealed chamber (3) containing a gas, in particular ozone, as the fundamental optical means.

6 Claims, 1 Drawing Sheet

INTRAOCULAR LENS

FIELD OF THE INVENTION

The present invention relates to an intraocular lens suited for implantation in the anterior or posterior chamber of the eye as a substitution for the natural lens.

DESCRIPTION OF THE PRIOR ART

The problem of optic compensation in the aphakic eye, that is an eye missing the natural lens, through implantation of an artificial lens has been approached, until now, with the utilization of intraocular lenses (I.O.L.), placed either in the anterior or posterior chamber of the eye. Intraocular lenses, of various designs and conceptions, have in common an "optic disk" of an average diameter comprised between 5 and 7 mm and a setting device formed by pins or points for securing the optic disk to the ocular structure.

All of the known intraocular lenses, from the optical standpoint, are composed of a plano-convex, biconvex or meniscus lens, in bio-tolerant plastic material, such as PMMA CQ (polymethylmethacrylate of clinical quality). Their optical function is that of correcting the aphakic eye introducing into it a dioptric power comprised between $-6.00$ D and $+30.00$ D, depending on the case.

The optic calculation of intraocular lenses is carried out on the basis of pre-operative surveys, such as keratometry and echobiometry, and analysis of the data with commonly used formulas of various authors.

Recently, bifocal and multifocal intraocular lenses have been made to allow the operated patient a sharp defined vision from close up without the use of glasses.

This method of correction of the aphakic eye introduces optical aberrations, well known to specialists in the field, which create considerable discomfort. With regard to the absorption of ultraviolet radiation, the problem is currently resolved by incorporating appropriate pigments into the material of the lenses. Furthermore, the intraocular lenses have a specific gravity greater than that of the medium (aqueous humour) in which they are placed, and as a result of the force of weight to which they are subjected, they can become dislocated causing those clinical pictures known as "setting sun" and "windshield wiper".

The main object of the present invention is to provide a newly conceived intraocular lens for the compensation of the dioptric conditions of the aphakic eye which accomplishes a marked reduction of the main optical-geometric aberrations and which is able to absorb ultraviolet radiation without the use of special or treated materials.

A further object of the present invention is to provide an intraocular lens of the above-mentioned type in which the effects of the force of weight upon it are null or negligeable.

A particular object of the present invention is to provide an intraocular lens of the above-mentioned type able to compensate the aphakic eye.

SUMMARY OF THE INVENTION

The intraocular lens according to the present invention allows for the accomplishment of the above-mentioned objects in that it comprises an optic disk and setting means for securing it to the ocular structure, and is characterized by the fact that said optic disk comprises two coaxial transparent elements, of an optically negligeable thickness, with different radius of curvature, coupled but with a space between them to delimit a sealed chamber containing a gas as the fundamental transparent optic medium. A particularly preferred gas for said application is ozone.

Further characteristics and advantages of the intraocular lens according to the present invention will be made apparent in the description which follows of one of its possible embodiments, given as an example but not limitative, with reference to the attached drawings.

BEST MODE OF CARRYING OUT THE INVENTION

Figure 2:
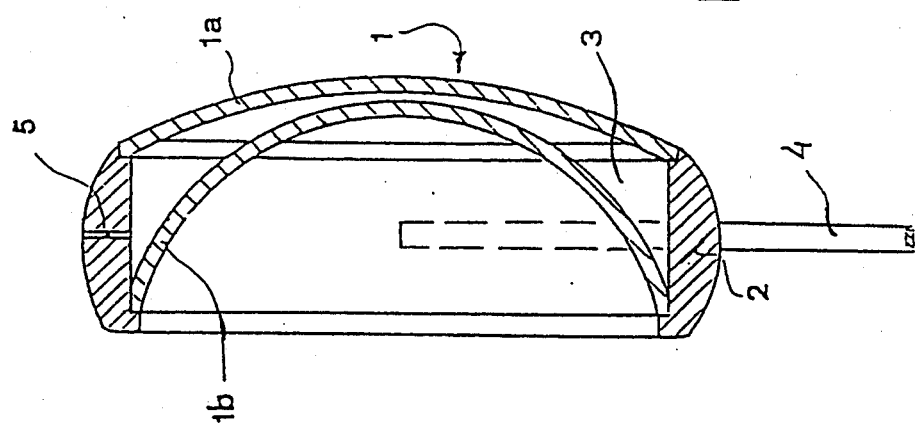
FIG. 2 is a sectional side view of the lens of FIG. 1.
Figure 1:
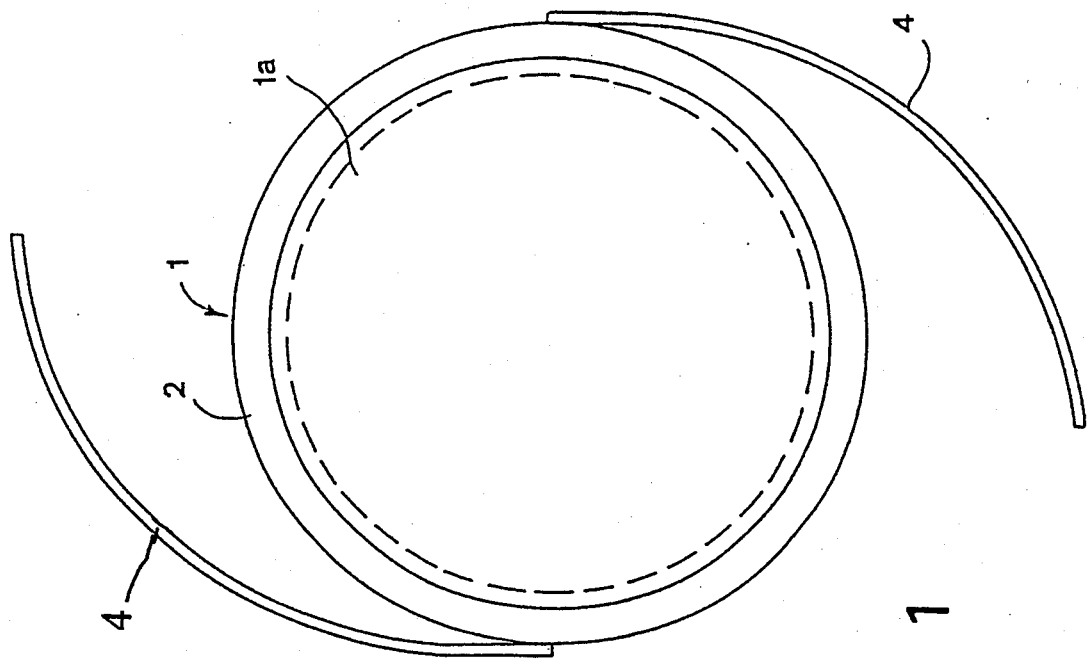
FIG. 1 is an enlarged front view of the intraocular lens according to the invention.

With reference to the above-mentioned figures, 1 indicates an optic disk with a convex anterior face or transparent curved surface 1a and a posterior concave face 1b coaxially coupled along the opposite edges of an assembly ring 2 to delimitate between them a sealed chamber 3, which in the present embodiment has the form of a meniscus. Then, indicated with 4, there are two pins of a conventional type for the securing of the lens to the ocular structure, each fixed with one of their respective ends to diametrically opposed points on the ring 2 and extending symmetrically with respect to the axis of the lens on its middle lying plane. For the securing of the pins 4 to the ring, taper holes can be made on the ring in which securing means with tapered ends pass, thus fixing the pins in such a way that they are resistant by traction.

The faces 1a and 1b can be formed with elements of optically negligeable thickness, whereas the fundamental optic medium is composed of a layer of ozone closed in a sealed chamber 3 and introduced therein by means of a valve 5. The form of the optic medium is therefore determined by the form of the chamber 3 which, in the embodiment illustrated, is a meniscus.

The choice of the gas ozone as the aeriform used as the fundamental optic medium is derived from the fact that it is substantially stable over time, transforming into oxygen in an extremely slow way, and it has the property of absorbing ultraviolet radiation, a particularly advantageous quality since it makes it possible to avoid recourse to special materials or materials incorporating pigments.

The lens, consisting of the faces 1a and 1b and the ring 2, can advantageously be made of non-toxic optically suitable material, such as the already mentioned P.M.M.A. C.Q., whereas the pins, in addition to the above-mentioned material, can be made of coated prolene, according to need, and fixed to the ring 2 by means of ultrasonic welding or other equivalent process. The diameter of the optic disk 1 can be 6 mm for implantation in the posterior chamber and 5 mm for implantation in the anterior chamber, with iris or iris-capsule fixing techniques.

The intraocular lens according to the present invention offers the possibility of being engaged after any surgical technique of removal of the natural lens, both as primary and secondary implant, provided that it is clinically possible.

The best optical solution in approaching the problem of geometric aberrations in an effective way is that of forming an optic disk 1 in the form of a meniscus. It is however clear that the section of the optic disk can also be biconcave, plano-concave, biconvex, etc.. The curvature values of the faces 1a and 1b are determined case by case according to the indications provided by the surgeon on the basis of the expected post-operative keratometry, the echobiometry and the position of the implant.

With appropriate variations of the active faces according to known techniques, it is possible to obtain intraocular lenses according to the invention also of bifocal and multifocal types in addition to the monofocal type. Intraocular lenses according to the present invention can be produced with methods and technologies already known. The first step, for example, can be the construction of optic meniscis (anterior and posterior face) in the monofocal, bifocal or possibly multifocal forms by the normal techniques used with contact lenses (turning and polishing, direct polymerization in molds, forming). Then, for instance by polymerization in molds, the assembly ring 2 is made, wherein a hole is formed for the injection of ozone. The two faces are then welded to the ring by ultrasound means or with liquid P.M.M.A. allowed to polymerize in the cleaned and polished contact zones. The pins 4 then are welded and the ozone is injected into the camber 3 through hole 5 which is then closed hermetically.

Alternatively, the assembly ring 2 can be formed directly by processing it in a single piece with the anterior face 1a or with the posterior one 1b in such a way that a single welding connection is necessary. The assembly of the lens can also be carried out inside an air-tight chamber containing ozone, thus elminating the necessity of injection of the ozone and of the relative valve.

The intraocular lens according to the present invention accomplishes the pre-determined objects. In fact thanks to the use of ozone gas as the fundamental optic medium, it is possible to obtain a complete absorption of the ultraviolet radiation without the use of pigments incorporated in the material composing the lens. Furthermore the presence of the sealed chamber containing the gas makes the lens extremely light and therefore much less influenceable by the force of weight, leading to consequently greater stability of the implant and reduction of the risk of its dislocation or subdislocation, as well as minimum stress of the anatomical structure concerned by the pins.

The chamber also allows complete compensation of the dioptric condition of the aphakic eye effectively and without aberrations. The geometric aberrations are eliminated because it is possible to calculate the curvature of the anterior and posterior faces in such a way that the geometric theory of first order optic radiation (Gauss approximation and Weiserstrass aplanatism) is applicable to them, something which is not possible in known I.O.L.'s. Thanks to this possibility also the correction of presbyopia is obtained in an optimum way. In bifocal and multifocal lenses, even if made with traditional techniques, it is in fact possible to obtain the same ideal optic conditions for the zone of close vision which are obtained in the zone destined to long-distance vision.

I claim:

1. Intraocular lens comprising an optic disk (1) and setting means (4) for securing it to an ocular structure, said optic disk (1) comprising a first and a second face (1a,b) which are coaxial and spaced apart, of an optically negligeable thickness and of different radii of curvature, coupled to delimitate between them a sealed chamber (3) containing ozone gas as the fundamental transparent optical medium.

2. Intraocular lens according to claim 1 wherein said chamber (3) is in the form of a meniscus to obtain the condition of aplanatism.

3. Intraocular lens according to claim 2 wherein said faces (1a,b) are connected to one another by means of an assembly ring (2) on which a sealable passage (5) is formed for the injection of said ozone gas.

4. Intraocular lens comprising an optic disk (1) and setting means (4) for securing it to an ocular structure, said optic disk (1) comprising a first and a second face (1a, b) which are coaxial and spaced apart, of an optically negligeable thickness and of different radii of curvature, coupled to delimitate between them a sealed chamber (3) containing gas as the fundamental transparent optical medium, said faces (1a, b) are connected to one another by means of an assembly ring (2) on which a sealable passage (5) is formed for the injection of said gas.

5. Intraocular lens according to claim 1 wherein said faces (1a,b) are connected to one another by means of an assembly ring (2) on which a sealable passage (5) is formed for the injection of said ozone gas.

6. Intraocular lens according to claim 4, wherein said chamber (3) is preferably in the form of a meniscus to obtain the condition of aplanatism.

* * * * *